United States Patent [19]
Lovey et al.

[11] Patent Number: 5,883,097
[45] Date of Patent: Mar. 16, 1999

[54] SOLUBLE AZOLE ANTIFUNGAL SALT

[75] Inventors: Raymond G. Lovey, West Caldwell; Viyyoor M. Girijavallabhan, Parsippany; Anil K. Saksena; Bruce E. Reidenberg, both of Upper Montclair, all of N.J.

[73] Assignee: Schering Corporation, Kenilworth, N.J.

[21] Appl. No.: 61,502

[22] Filed: Apr. 16, 1998

[51] Int. Cl.$^6$ .................. A61K 31/495; C07D 405/14
[52] U.S. Cl. .................................. 514/252; 544/366
[58] Field of Search ............... 514/252; 544/366

[56] References Cited

U.S. PATENT DOCUMENTS 5,714,490  2/1998  Saksena et al. .................. 514/252

*Primary Examiner*—Michael G. Ambrose
*Attorney, Agent, or Firm*—Thomas D. Hoffman

[57] ABSTRACT

The lactic acid[$CH_3CH(OH)CO_2H$] addition salt of the compound of formula I

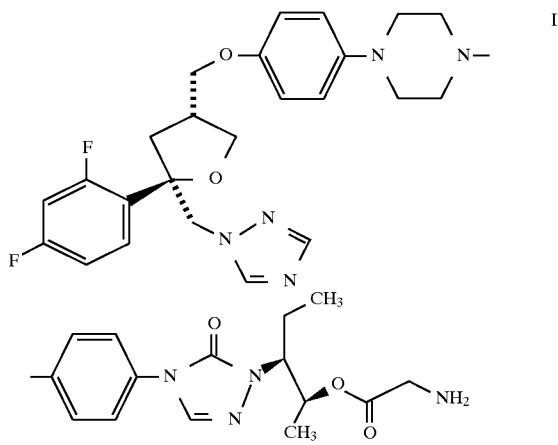

wherein the molar ratio of lactic acid, preferably L-lactic acid, to the compound of formula I is preferably about 1:1, pharmaceutical compositions of the lactic acid addition salt in an aqueous lactic acid carrier suitable for intravenous administration, and methods of using either of them to treat and/or prevent susceptible fungal infections in a host such as a mammal are disclosed.

18 Claims, No Drawings

SOLUBLE AZOLE ANTIFUNGAL SALT

BACKGROUND OF THE INVENTION

This invention relates to a water soluble lactic acid addition salt of (-)-[(2R)- cis]-4-[4-[4-[4-[[-5-(2,4-difluorophenyl)-tetrahydro-5-(1 H-1 ,2,4-triazol-1-ylmethyl)-3-furanyl]methoxy]phenyl]-1 -piperazinyl] phenyl]-2,4-dihydro-2-[1 (S)-ethyl-2(S)-hydroxpropyl]-3H-1,2,4-triazol-3-one, pharmaceutical compositions containing the lactic acid addition salt in pharmaceutically acceptable carrier such as aqueous lactic acid as well as methods of treating and/or preventing susceptible fungal infections in a host including mammals especially humans with said lactic acid addition salt.

Systemic fungal infections are becoming a serious and potentially fatal problem in immunocompromised patients. Such patients have a compromised or suppressed immune system due to immunosuppression therapy following organ transplant, use of cytotoxic drugs for treatment of cancer or HIV infections. Injectable antifungal agents such as Amphotericin B are active against a wide variety of fungi but exhibit significant toxic side effects. The azole antifungals fluconazole, itraconazole and ketoconazole can be administered orally or via injection but have more limited antifungal activity th an Amphotericin B. In addition, prolonged exposure to antifungals agents has resulted in increased fungal resistance to some of these agents.

Thus, there is a need for a broad spectrum antifungal agent having activity against fungi such as Aspergillus and *Candida krusei* resistant to existing anti- fungal agents and which is capable of being administered intravenously.

International Publication No. PCT/EP/00174, published 27 Jul. 1995 discloses azole tetrahydrofuran and dioxolane antifungals, but not the lactic acid addition salt of this invention.

International Publication No. WO 95/17407 published 29 Jun. 1995 discloses various (2 R-cis)-4-[4-[4-[4-[[-5-(2,4-difluorophenyl)-tetrahydro-5-(1 H-1,2,4-triazol-1-ylmethyl)-3-furanyl]methoxy]phenyl]-1 -piperazinyl] phenyl]2,4-dihydro-2-[mono- or dihydroxy($C_3$–$C_8$) alkyl]-3 H-1,2,4-triazol-3-one substituted antifungals, esters, ethers and salts thereof. The hydrochloride salt of the glycine ester of (-)-[(2 R)-cis]-4-[4-[4-[4-[[-5-(2,4-difluorophenyl)-tetrahydro-5-(1 H-1,2,4-triazol-1 -ylmethyl)-3-furanyl] methoxy]phenyl]-1 -piperazinyl]phenyl]-2,4-dihydro-2-[1 (S)-ethyl-2(S)-hydroxypropyl]-3 H-1,2,4-triazol-3-one is disclosed in U.S. Pat. No. 5,714,490. There is no disclosure in the above-listed patent or patent applications of the specific monolactic acid addition salt or the specific pharmaceutical compositions of the present invention.

SUMMARY OF THE INVENTION

We have discovered that the lactic acid [$CH_3CH(OH)CO_2H$] addition salt of the compound represented by formula I

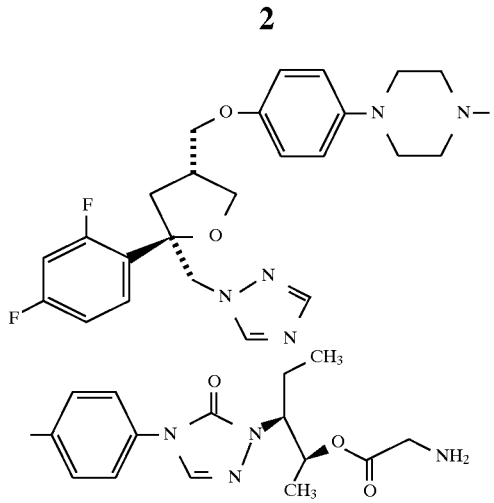

is surprisingly soluble in pharmaceutically acceptable carriers especially aqueous lactic acid solutions to provide a pharmaceutical composition suitable for intravenous use. In the preferred the lactic acid addition salt of the present invention, the molar ratio of lactic acid to the compound of formula I is about 1:1.

Thus, the present invention also provides pharmaceutical compositions comprising an antifungally effective amount of a lactic acid [$CH_3CH(OH)CO_2H$] addition salt of the compound of formula I together with a pharmaceutically acceptable carrier. The preferred pharmaceutically acceptable carrier is an aqueous lactic acid solution, more preferably one wherein the molar ratio of lactic acid to the compound of formula I is in the range of about 6:1 to 70:1.

The present invention further provides methods of treating and/or preventing susceptible fungal infections in a host such as mammals, especially humans afflicted with such fungal infections by administering an anti-fungally effective amount of the lactic acid salt of the compound of formula I together with a pharmaceutically acceptable carrier sufficient for such treating and/or preventing. The preferred lactic acid used in this invention is L-lactic acid but use of D- or D/L-lactic acid is also considered within the scope of this invention.

DETAILED DESCRIPTION OF THE INVENTION AND OF THE PREFERRED EMBODIMENTS

The monohydrochloride salt of the compound of formula I disclosed in commonly-owned U.S. Pat. No. 5,714,490 is sparingly soluble in water. Only 1–2 mg of the hydrochloride salt dissolves in 1 mL of water, and unacceptably large volumes of water would be required for delivery of an effective dose. Furthermore, only in an aqueous hydrochloric acid solution at the physiologically unacceptable pH of 1–1.5 does enough of the hydrochloride acid addition salt of the compound of formula I dissolve to provide a suitably concentrated solution useful for intravenous use.

During the development of this invention, the use of inorganic acids (e.g. HBr, $H_2SO_4$ and $H_3PO_4$) and various organic acids (e.g. malic, citric and tartaric acids) to form acid addition salts was investigated. None of these inorganic or organic acids formed a pharmaceutically acceptable acid addition salt with a suitable aqueous solubility at a physiologically acceptable pH of greater than about 3.0–3.5. A suitable aqueous solubility for a therapeutic agent such as the lactic acid addition salt of this invention useful for intravenous administration is at least about 2 mg of said salt/ml, preferably about 20 to 30 mg/ml at a physiologically acceptable pH, i.e. a pH of at least than about 3 to 3.5.

Surprisingly we have discovered that the lactic acid addition salt of the compound of formula I is soluble in aqueous lactic acid solution at a physiologically acceptable pH of at least about 3 to 3.5 to provide commercially feasible concentrated pharmaceutical compositions suitable for parenteral administration for effectively treating and/or preventing susceptible fungal infections in a host such as a mammal, especially humans.

The molar ratio of lactic acid to the compound of formula I is about 0.7:1 to about 3:1, preferably about 1:1. The pharmaceutical compositions of this invention comprises the lactic acid addition salt of the compound of formula I in the molar ratio of about 0.7:1 to about 3:1, preferably about 1:1, together with a pharmaceutically acceptable carrier which is preferably aqueous lactic acid wherein the molar ratio of total lactic acid in the composition to the compound of formula I is about 6:1 to 70:1 and preferably is about 50:1.

The lactic acid addition salt of the compound of formula I is readily convertible in vivo into the corresponding alcohol of formula II.

and in a *Candida albicans* (four strains) systemic model with normal and compromised mice (PO-1 XDX4D) compared to other azoles, e.g. fluconazole.

The in vivo oral antifungal activity of the compound of formula II was compared to azole antifungals, e.g., fluconazole in an Aspergillus pulmonary infection model in mice. The procedure of David Loebenberg et al. entitled "In vitro and In vivo Activity of Sch 42427, The Active Enantiomer of the Antifungal Agent Sch 39304", *Antimicrobial Agents and Chemotherapy,* (1992), 36, 498–501 was used. The Aspergillus flavus pulmonary model is also described in European Patent Application No. 0539,938 Al published on 5 May 1993.

The compound of formula II also exhibited superior antifungal in vitro activity in SDB against 37 species of Aspergillus with (a) geometric mean MIC of 0.096 compared to fluconazole (geometric mean MIC$\geq$32 and (b) with geometric mean MFC compared to fluconazole (geometric mean MFC$\geq$32).

The compound of formula II showed consistently higher serum levels in mice, rats, dogs and monkeys following oral dosing with a methyl cellulose formulation compared to

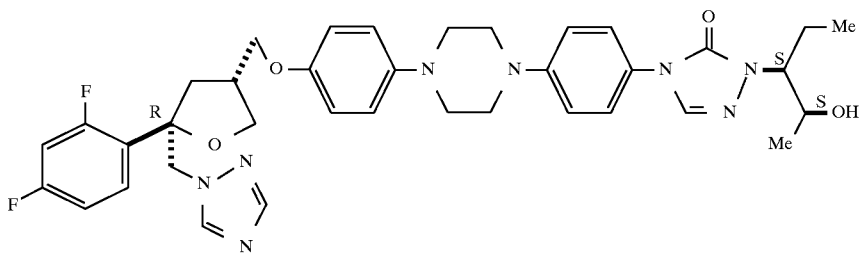

The compound of formula II exhibits a broad spectrum antifungal activity in various in vitro assays against Candida, other yeasts, dematophytes, Aspergillus and opportunistic fungi. The in vitro antifungal activity tests were performed via conventional broth dilution methods in Sabouraud dextrose broth ("SDB") medium and Eagles Minimum Essential Medium ("EMEM") against a large number of fungi. Minimum Inhibitory Concentrations ("MICs") were measured after 24, 48 and 72 hour tests. In many cases, Minimum Fungicidial Concentrations ("MFCS") were measured after 48 and 72 hours.

The term "opportunistic fungi" include Cryptococcus, Histoplasma, Blastomyces, Coccidioides, Fusarium, Mucor, Paracoccidioides, Fonsecaea, Wangiella, Sporothrix, Pneumocystis, Trichosporon as shown by in vivo activity in an appropriate animal species e.g. mouse, rat or rabbit. The compounds of the inventions are expected to exhibit activity against many genera and species of protozoa, bacteria, gram negatives, gram positives, anaerobes, including Legionella Borrelia, Mycoplasma, Treponema, Gardneralla, Trichomononas and Trypanosoma The compound of formula II exhibited (1) superior antifungal activity as measured by geometric mean MICs and MFCs in various in vitro assays against *C. albicans* (N=26), *C. krusei* (N=16), *C. glabrata* (N=9), *C. tropicalis* (N=4), *C. stellatoidea* (N=1), *C. neoformans* (N=3), and of the dermatophytes, *T. rubrum, T. mentagrophytes,* and *T. tonsurans* (N=6) (after 48 or 78 hours) compared to fluconazole as well as (2) superior anti-fungal activity in the following in vivo models: an Aspergillus flavus and fumigatus (four strains) in a pulmonary immuno-compromised mouse model (PO-1XDX4D) compared to other azoles e.g. itraconazole, azoles of similar structure and also exhibited very long serum half lives following O.D. dosing with good tissue distribution. The compound of formula II is not an inducer of various cytochrome P-450 liver drug metabolizing enzymes after oral administration in an in vivo rat model.

The preferred pharmaceutically acceptable mono-lactic acid addition salt of this invention is formed by adding to a solution of the compound of formula I in an aprotic solvent such as THF about a stoichiometric amount of lactic acid, e.g., L-lactic acid in an aprotic solvent, e.g.,THF. A non-polar solvent, e.g. hydrocarbon solvent such as, hexane, was added to the so formed mixture and the precipitated salt was recovered using standard filtration techniques.

The compound of formula I may be prepared by reaction of N-Cbz or N-Boc-glycine with the compound of formula II (prepared in accordance with the procedures of Examples 24 or 32 of International Publication No. WO 95/17407, published 29 Jun. 1995) in the presence of dimethylaminopyridine (DMAP) and dicyclohexylcarbodiimide (DCCD) in an aprotic solvent e.g. $CH_2Cl_2$ at 0° to 25° C. The nitrogen protecting groups (Cbz or Boc) are removed by use of conventional synthetic techniques well known to those skilled in the art to provide the compound of formula I.

The pharmaceutical compositions of the present invention may be adapted for any mode of administration e.g., for oral, parenteral, e.g., SC, IM, IV and IP, topical or vaginal administration or by inhalation (orally or intranasally). Such compositions are formulated by combining the lactic acid addition salt of the compound of formula I with a suitable, inert, pharmaceutically acceptable carrier or diluent.

Examples of suitable compositions include solid or liquid compositions for oral administration such as tablets, capsules, pills, powders, granules, solutions, suppositories, troches, lozenges, suspensions or emulsions. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided lactic acid addition salt of the compound of formula I. In the tablet, the acid addition salt of compound of formula I is mixed with carrier having the necessary binding properties in suitable proportions and compacted in the shape and size desired.

Topical dosage forms may be prepared according to procedures well known in the art, and may contain a variety of ingredients, excipients and additives. The formulations for topical use include ointments, creams, lotions, powders, aerosols, pessaries and sprays.

For preparing suppositories, a low melting wax such as a mixture of fatty acid glycerides or cocoa butter is first melted, and the active ingredients are dispersed homogeneously therein as by stirring. The molten homogeneous mixture is then poured into convenient sized molds, allowed to cool and thereby solidify.

Liquid form preparations include solutions formed by dissolving the lactic acid addition salt of the present invention with aqueous lactic acid solvent wherein the molar ratio of lactic acid to water is in the range of about 6:1 to 70:1. The preferred liquid formulation are prepared using L-lactic acid for the acid addition salt as well as for the lactic acid used in the aqueous lactic acid solvent.

The pharmaceutical compositions of the present invention may be prepared by admixing the pharmaceutically acceptable carrier, e.g., the aqueous lactic acid solvent, and adding thereto an antifungally effective amount of the lactic acid addition salt of the compound of formula 1. The solution so formed is optionally filtered. The formation of the solution may take place at a temperature of about 15° to 35° C. The water is normally sterilized water and may also contain pharmaceutically acceptable salts and buffers, e.g., phosphate or citrate as well as preservatives.

Also included are solid form preparations which are intended to be converted, shortly before use, into liquid form preparations for either oral or parenteral administration. The solid form preparations intended to be converted to liquid form may contain, in addition, to the active materials, such as compounds of this invention, and optionally a cell wall active compound, especially a fungal cell wall inhibitor, e.g., a nikkomycin, flavorants, colorants, stabilizers, buffers, artificial and natural sweeteners, dispersants, thickeners, solubilizing agents and the like. The solvent utilized for preparing the liquid form preparations may be water, isotonic water, ethanol, glycerin, polyethylene glycols, propylene glycol, and the like, as well as mixtures thereof.

Parenteral forms to be injected intravenously, intramuscularly, or subcutaneously are usually in the form of a sterile solution, and may contain salts or glucose to make the solution isotonic.

The topical dosage for humans for antifungal use in the form of a pharmaceutical formulation comprising the lactic acid addition salt of the compound of formula I (usually in the concentration in the range from about 0.1% to about 20% preferably from about 0.5% to about 10% by weight) together with a non-toxic, pharmaceutically acceptable topical carrier, is applied daily to the affected skin until the condition has improved.

In general, the oral dosage for humans for antifungal use ranges from about 1 mg per kilogram of body weight to about 30 mg per kilogram of body weight per day, in single or divided doses, with about 1 mg per kilogram of body weight to about 20 mg per kilogram of body weight per day being preferred and the dose of about 1 mg per kilogram of body weight to about 10 mg per kilogram of body weight per day being most preferred.

In general, the parenteral dosage for humans for antifungal use ranges from about 0.25 mg per kilogram of body weight per day to about 20 mg kilogram of body weight per day, in single or divided doses, with about 0.5 to about 10 mg per kilogram of body weight per day being preferred.

The exact amount, frequency and period of administration of the acid addition salt of the of formula I of the present invention for antifungal use will vary, of course, depending upon the sex, age and medical condition of the patent as well as the severity of the infection as determined by the attending clinician.

GENERAL EXPERIMENTAL

The starting materials and reagents used herein are commercially available or readily made by one skilled in synthetic organic chemistry.

EXAMPLE 1

-(2 R-cis)-4-[4-[4-[4-[[-5-(2,4-Difluorophenyl)-tetrahydro-5-(1 H-1,2,4-triazol-1 -ylmethyl)furan-3-yl]methoxy] phenyl]-1 -piperazinyl]phenyl]-2-4-dihydro-2-[(1 S)-ethyl-2(S)-hydroxypropyl]-3 H- 1,2,4-triazol-3-one.

a. The methyl ester of (S)-lactic acid was converted into the corresponding benzyloxymethyl ether in accordance with the procedure of W. C. Still, et al. Tetrahedron Letters, 21, 1035–1038 (1980).

b. Reduction to the Aldehyde

DIBAL-H, 37.7 ml of a 1 M solution, was added dropwise to a stirred solution of 7.67 g of the ester of step (a) of this Example in toluene at −78° C. (dry ice/acetone bath) under an atmosphere of nitrogen. After 6 min. methanol (10 ml) followed by an aqueous solution of Rochelles salt were added. After warming to room temperature the moisture was partitioned between EtOAc and water. The organic phase was separated, washed with water, dried ($MgSO_4$) and concentrated to produce the crude aldehyde which was used in the next step without purification.

b. Grignard Step

The THF solution of 80 ml of 1 molar solution of the ethyl magnesium bromide Grignard reagent was added dropwise to a stirred THF solution of the crude aldehyde obtained from step (b) of this Example at −78° C. (dry ice/acetone bath) under an atmosphere of nitrogen. After the addition was complete, the resulting mixture was allowed to warm slowly to room temperature overnight and stirred for a further period of 48 h. An aqueous solution of Rochelles salt was added and then the resulting mixture was partitioned between acetone and water. The organic phase was separated, washed with water, dried ($MgSO_4$) and concentrated. The residue was purified by column chromatography on silica gel using EtOAc/Hexane (1:10) as eluant to give (i) non-polar alcohol (2 S,3 S) 2.31 g;31%, as a colorless oil.

(ii) a mixture of both alcohols, 1.23 g; 41% and (iii) polar alcohol (2 S,3 R) 1.23 g; 16%, as a colorless oil.

c. Brosylation of polar alcohol

4-Bromobenzenesulphonyl chloride (1.035 g, 4.1 mmoles) was added to a stirred solution of (0.605 g, 2.7 mmoles) the polar (2 S, 3 R) alcohol of step (b) of this Example and 2.20 g (5.9 mmoles) of DMAP in $CH_2Cl_2$ at room temperature under an atmosphere of nitrogen. The resulting mixture was stirred for 12 h. and then partitioned between EtOAc and water. The organic phase was separated, washed with water, dried and concentrated. The residue was purified by column chromatography on silica gel using EtOAc/Hexane (1:10) as eluant to give the desired brosylate (85%) as a colorless oil.

d. Alkylation and acidic hydrolysis

The procedures of Example 18(c) and (d) of International Publication No. WO/17407 ,published 29 Jun. 1995 were followed except the (2 S, 3 R) biosylate of step (c) of this Example was substituted for that used in Example 18(c). The acidic hydrolysis produced the title compound as a white solid, mp 170°–172° C.

EXAMPLE 2

(-)-[(2 R)-cis]-4-[4-[4-[4-[[5-(2,4-Difluorophenyl)-Tetrahydro-5-(1 H-1,2,4-Triazol- 1 -ylmethyl)-3-Furanyl] Methoxy]Phenyl]-1 -Piperazinyl]Phenyl]-2,4-Dihydro-2-[1 (S)-Ethyl-2(S)-Hydroxypropyl]-3 H-1,2,4-Triazol-3-one, Ester with Glycine (as Hydrochloride) .

a. To a solution of N-Cbz-glycine (315 mg), N,N-dimethylaminopyridine (DMAP, 200 mg), and compound of Example 1 (900 mg) in CH$_2$Cl$_2$ (50 mL) at 0° C., add dicyclohexylcarbodiimide (DCCD, 290 mg).

Stir the solution at 0° C. for 30 min., then at room temperature for 1 hr. Add additional N-Cbz-glycine (700 mg) and then increments of DCCD at 20 min. intervals until the reaction is complete by TLC. Pour the reaction mixture into 5% aqueous KH$_2$PO$_4$ and extract with EtOAc. Wash the EtOAc extracts three times with 5% aqueous KH$_2$PO$_4$, then with brine, and dry the extracts over anhydrous MgSO$_4$. Filter, evaporate the filtrate, and chromatograph the residue to obtain the N-Cbz-glycinyl ester (1.3 g). [Mass spec. found: (FAB) 892 (M+H$^+$).]

b. Stir a solution of the N-Cbz-glycinyl ester of step A above in 100 mL MeOH-96% HCOOH (10:1) in sealed flask with a safety valve. Add 30 mg increments of palladium black at 30 min intervals until the reaction is complete by TLC (6–14 hr.). Suction-filter the mixture, add 12N HCl (0.5 mL) to the filtrate and evaporate the so-formed mixture to dryness. Add water (100 mL) and activated carbon (0.8 g) to the residue, suction-filter on a 0.45$\mu$ nylon membrane. Lyophilize the filtrate to provide 356 mg of the title compound. [Mass spec. found: (FAB) 795 (M+H$^+$).]

EXAMPLE 3

Follow the procedure of Example 2 except substitute an equivalent amount of the N-tert-butoxycarbonyl protected (BOC)-lactic acid to obtain the corresponding N-BOC-glycinyl ester. Treat the N-BOC-glycinyl ester with 4N Hcl-dioxane solution. Evaporate the solvent, add water to the residue and suction-filler on a 0.45$\mu$ nylon membrane. Lyophylize the filtrate to obtain the title compound of Example 2.

EXAMPLE 4

(-)-[(2 R)-cis]-4-[4-[4-[4-[[5-(2,4-Difluorophenyl)-Tetrahydro-5-(1 H-1,2,4-Triazol-1-ylmethyl)-3-Furanyl] Methoxy]Phenyl]-1 -Piperazinyl]Phenyl]-2,4-Dihydro-2-[1 (S)-Ethyl-2(S)-Hydroxypropyl]-3 H-1,2,4-Triazol-3-one, Ester with Glycine (as the L-Lactic acid salt).

A. Partition 250 mg of the hydrochloride salt of Example 2 with saturated aqueous solution of NaHCO$_3$/—CH$_2$Cl$_2$. Separate the layers and filter the organic phase through a cotton plug. Add toluene and remove the solvents under reduced pressure with a rotary evaporator. Add ethyl ether to the so-formed residue. Triturate the slurry and filter the organic phase. Remove the organic solvent under vacuum to leave the free base of the glycine ester of Example 2.

B. Dissolve 697 mg (0.92 mmol) of the compound of paragraph A of ths Example in 40 ml of THF by applying gentle heating. To the so-formed solution, add a solution of 100 mg (1.109 mmol) of L-lactic acid (available from Sigma Chemical Co.) in 4 ml of THF. To the stirred, so-formed solution add 35 ml of n-hexane. Allow the so-formed reaction mixture to stand for 18 hrs. at room temperature. Decant the supernate from the so-formed precipitate. Upon drying the precipitate there was obtained 631 mg of the titled L-lactic acid addition salt.

H$^1$ NMR (DMSO-d$_6$) (300 MHz): δ8:34(s,2), 7.78(s,1), 7.48(d,z), 7.28(m,2), 7.1 0(d,2),6.98(m,1),6.93(d,2),6.79(d, 2),5.08(p,1)4.56(dd,2),3.98(m),3.70(m),3.43(dt, 1)3.30 (m.4),3.15(m,4),2.45(mm),2.12(dd,1),1.76(m,2);1.22(d,3), 1.1 9(d,3),0.77(t,3).

What is claimed is:

1. A lactic acid [CH$_3$CH(OH)CO$_2$H] addition salt of the compound represented by formula I

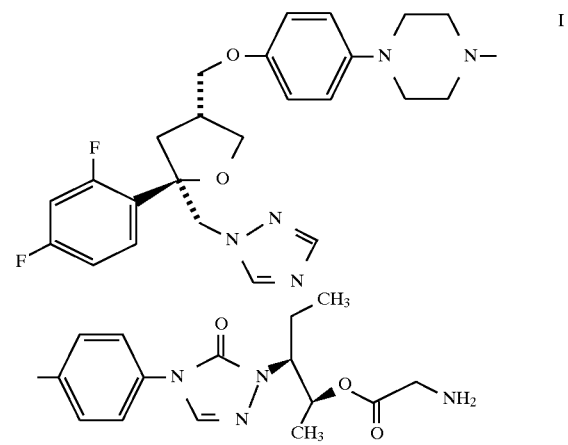

2. The lactic acid addition salt of claim 1 wherein the molar ratio of lactic acid to the compound of formula I is about 1:1.

3. The lactic acid addition salt of claim 1 wherein L-lactic acid is used.

4. A pharmaceutical composition comprising an antifungally effective amount of the lactic acid addition salt of the compound of formula I of claim 1 together with a pharmaceutically acceptable carrier.

5. The pharmaceutical composition of claim 4 wherein the molar ratio of lactic acid to the compound of formula I is about 1:1.

6. The pharmaceutical composition of claim 4 wherein the pharmaceutically acceptable carrier is aqueous lactic acid wherein the molar ratio of lactic acid to the compound of formula I is about 6:1 to 70:1.

7. The pharmaceutical composition of claim 4 wherein the molar ratio of lactic acid to the compound of formula I is about 50:1.

8. A pharmaceutical composition comprising an anti-fungally effective amount of the lactic acid addition salt of the compound represented by the formula I of claim 1 together with a mixture of lactic acid and water wherein the molar ratio of lactic acid to the compound of formula I is in the range of about 6:1 to 70:1.

9. The pharmaceutical composition of claim 8 adapted for intravenous administration.

10. The pharmaceutical composition of claim 8 wherein the lactic acid used is L-lactic acid.

11. A method of treating and/or inhibiting a fungal infection in a host in need of such treating and/or preventing which comprises administering an anti-fungally effective amount of a lactic acid addition salt of a compound of formula I of claim 1 sufficient for such treating and/or inhibiting together with a pharmaceutically acceptable carrier.

12. The method of claim 11 wherein the molar ratio of lactic acid to the compound of formula I in the acid addition salt is about 1:1.

13. The method of claim 11 wherein the pharmaceutically acceptable carrier is aqueous lactic acid.

14. The method of claim 11 wherein the acid addition salt is administered orally.

15. The method of claim 11 wherein the acid addition salt is administered parenterally.

16. The method of claim 11 wherein the acid addition salt is administered intravenously.

17. The method of claim 11 wherein the acid addition salt is administered intramuscularly.

18. The method of claim 11 wherein the acid addition salt is administered subcutaneously.

* * * * *